United States Patent [19]

Cates et al.

[11] Patent Number: 4,568,445
[45] Date of Patent: Feb. 4, 1986

[54] ELECTRODE SYSTEM FOR AN ELECTRO-CHEMICAL SENSOR FOR MEASURING VAPOR CONCENTRATIONS

[75] Inventors: Marion H. Cates, Largo; Eugene L. Szonntagh, N. Largo, both of Fla.

[73] Assignee: Honeywell Inc., Minneapolis, Minn.

[21] Appl. No.: 685,104

[22] Filed: Dec. 21, 1984

[51] Int. Cl.$^4$ .............................................. G01N 27/46
[52] U.S. Cl. ................................... 204/415; 204/416; 204/418; 204/419; 204/435
[58] Field of Search ................................ 204/415–420, 204/435.1 P

[56] References Cited

U.S. PATENT DOCUMENTS

| | | | |
|---|---|---|---|
| 3,556,950 | 1/1971 | Dahms | 204/419 |
| 3,672,962 | 6/1972 | Frant et al. | 204/419 |
| 3,740,326 | 6/1973 | Grubb | 204/418 |
| 3,915,831 | 10/1975 | Riseman et al. | 204/419 |
| 3,997,420 | 12/1976 | Buzza | 204/415 |
| 4,020,830 | 5/1977 | Johnson et al. | 204/415 |
| 4,071,427 | 1/1978 | Cheng et al. | 204/419 |
| 4,161,437 | 7/1979 | Fleckenstein | 204/415 |
| 4,169,779 | 10/1979 | Tataria et al. | 204/415 |
| 4,250,010 | 2/1981 | Kondo et al. | 204/412 |
| 4,410,409 | 10/1983 | Harman | 204/415 |
| 4,437,970 | 3/1984 | Kitajima et al. | 204/416 |
| 4,450,064 | 5/1984 | Harman | 204/415 |
| 4,474,183 | 10/1984 | Yano et al. | 204/415 |

Primary Examiner—T. Tung
Attorney, Agent, or Firm—Mitchell J. Halista; Trevor B. Joike

[57] ABSTRACT

An electrode system for an electrochemical sensor has a plurality of electrically conductive sensing segments isolated from each other and mounted on a support substrate formed from a chemically inert encapsulation material. The sensing segments are unencapsulated and are each coated with respective ones of ion conducting sensing materials to characterize each of the segments except for one of the segments which is uncoated and is arranged to be used as a reference electrode. The outer surface area of the sensing materials and the reference electrode is coated with a layer of a nonaqueous electrolyte which serves as a sorption/desorption medium. The electrolyte, in turn, is covered by a semipermeable thin film membrane secured at its peripheral edge by an O-ring to the support to form a fluid seal. Electrically conductive leads are connected to respective ones of the sensing surfaces, and a temperature measuring device is provided in the electrode structure for temperature compensation.

10 Claims, 2 Drawing Figures

ELECTRODE SYSTEM FOR AN ELECTRO-CHEMICAL SENSOR FOR MEASURING VAPOR CONCENTRATIONS

BACKGROUND OF THE INVENTION

1. Field of the Invention

The present invention relates to electrochemical sensors. More specifically, the present invention is directed to an electrode for an electrochemical sensor for the measurement of vapor constituent concentration.

2. Description of the Prior Art

The conventional electrochemical detection of gases and vapors customarily used in apparatus for collecting the gases and vapors in bubblers, impingers, wetted foams, etc. The gases and vapors were thereby retained or dissolved in liquids that were subsequently analyzed by electrochemical methods, e.g., potentiometric, conductometric, Redox, etc. One such prior art device was the Leeds and Northrup "Thomas Autometer" which was used for $SO_2$ analysis. That device bubbled an atmosphere containing the $SO_2$ through a solution of sulfuric acid ($H_2SO_4$) and hydrogen peroxide ($H_2O_2$). The $SO_2$ was dissolved, i.e., absorbed, and oxidized into sulfuric acid. The additional sulfuric acid formed by this process increased the conductivity of the solution. This change in conductivity was measured by a conductometer, i.e., an electrolyte conductivity instrument. Such an apparatus is inherently incapable of being miniaturized to a hand-held or wrist-mounted size which is desirable to achieve maximum portability for field use. Further, the aforesaid prior art devices used separate trapping and measuring operations which significantly decreased the speed of analysis of the gases and vapors. Accordingly, it would be desirable to provide a gas analyzer suitable for extreme miniaturization while providing a rapid and substantially continuous gas analysis.

SUMMARY OF THE INVENTION

The object of the present invention is to provide an improved electrode for as electrochemical sensor.

In accomplishing this and other objects, there has been provided, in accordance with the present invention, an electrode for an electrochemical sensor system comprising a chemically inert non-conductive substrate, a plurality of electrically conductive segments isolated from each other mounted on the substrate, a plurality of differing ion conductive sensing materials covering respective ones of the segments, at least one electrically conductive uncoated segment mounted on the substrate and isolated from the plurality of segments, a non-aqueous electrolyte covering all of said segments on an outside surface of the sensing materials and on the uncoated segment to form a sorption/desorption medium, a semi-permeable membrane means covering the electrolyte and a plurality of electrical conductors attached to respective ones of the segments.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Detailed Description

Figure 1:
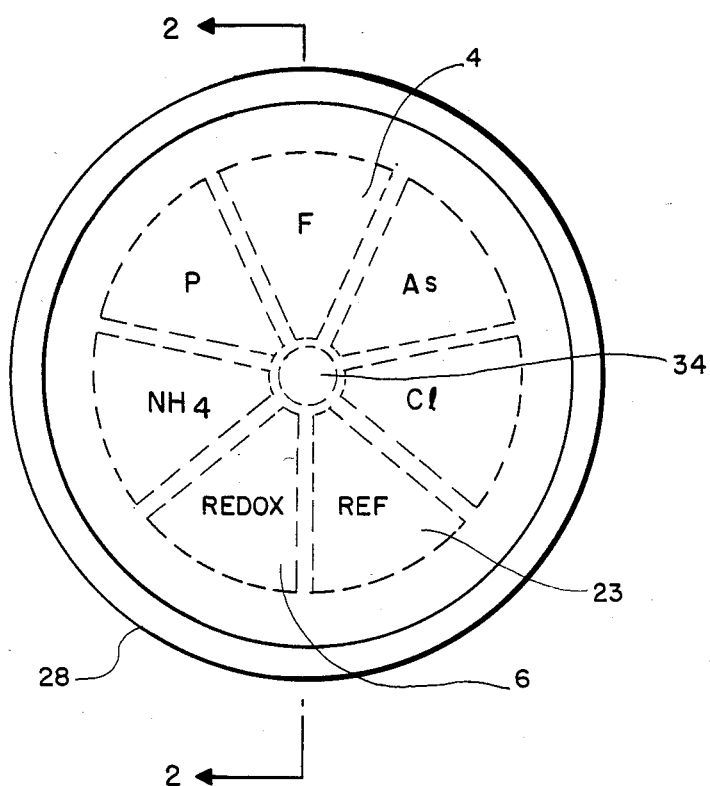
FIG. 1 is a pictorial illustration of the face of electrochemical sensor embodying an example of the present invention and FIG. 2 is a cross-sectional illustration of the sensor shown in FIG. 1 taken along section.lines 2—2.
Figure 2:
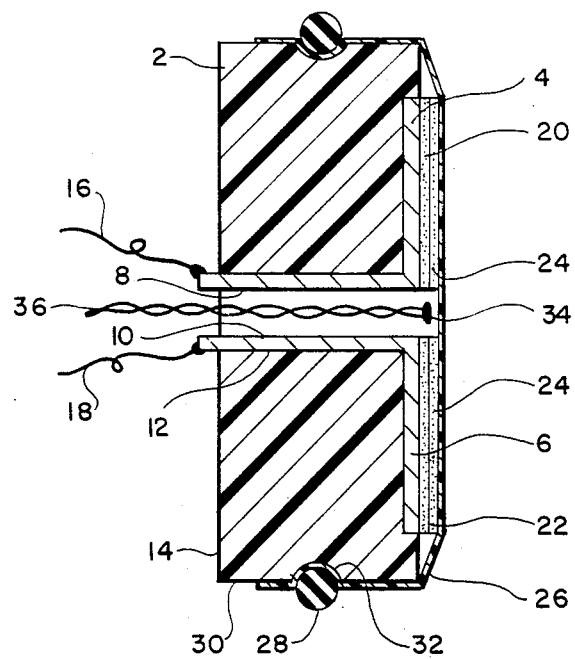

Referring to FIGS. 1 and 2 in more detail, there is shown, respectively, a face view and a cross-sectional side view of an electrochemical sensor embodying an example of the present invention and having a chemically inert substrate 2 for supporting a plurality of electrically conductive thin segments, e.g., segments 4 and 6 on an outer surface thereof. The substrate 2 can be made of a very high impedance glass-filled epoxy with a diameter of 5 to 25 mm and a thickness of 1 to 10 mm Each of the segments is arranged to have a circular wedge shaped surface with an electrically conductive extension extending through an opening in the substrate 2. For example, segments 4 and 6 have, respectively, extensions 8 and 10. The extensions 8 and 10 are arranged to extend through an axially aligned hole 12 in the substrate 2 and project past the back face 14 of the substrate 2. An electrical conductor is attached to each of the extensions, e.g., conductor 16 is attached to the extension 8 while a similar electrical conductor 18 is attached to the extension 10. All but one of the wedge shaped surfaces are coated with an appropriate ion conductive sensing material, e.g., segment 4 is coated with a sensing material 20 while segment 6 is coated with a sensing material 22. An uncoated segment 23 is used as a reference electrode.

A nonaqueous electrolyte layer 24 of approximately one mil thickness is arranged to cover all of the segments on the outside surface of any sensing material thereon, e.g., the sensing materials 20 and 22. A semi-permeable membrane 26, e.g., silcone rubber is used to cover the electrolyte 24 and is secured by an O-ring 28 to an outer edge 30 of the substrate 2 by having the O-ring 28 urge the membrane 26 into a semicircular groove 32 in the edge 30 of the substrate 2. A temperature measuring device, e.g., thermistor 34 is provided in the hole 12 adjacent to the membrane 26. A pair of leads 36 are provided o connect the thermistor 34 to associated equipment (not shown) to provide temperature compensation for the sensor. The hole 12 is filled with a chemically inert encapsulation material similar to that used for the substrate 2 to exclude continents from the sensing segments under the membrane 26.

The electrochemical sensor shown in FIGS. 1 and 2 allows gases and vapors in an atmosphere adjoining the membrane 26 to selectively permeate into the layer of the electrolyte 24 in which some constituents dissolve more than others. Desorption also occurs at a varying rate, resulting in an equalibrium concentration of atmospheric constituents in the nonaqeous electrolyte layer 24. A soon as higher concentrations develop outside of the electrode, the liquid layer would also acquire higher concentrations and vice versa. The adjoining solid state electrode segment selectively respond to various ions or an oxidation and reduction process is performed at the redox electrode. Thus, the sensor segments develop potential differences between the segment used a reference electrode and themselves.

The various electrode potentials of the multielectrode system are scanned by a conventional microprocessor and signal multiplexer (not shown) and by analyzing the responding electrode and the magnitude or potential of the developed signal, the microprocessor can substantially continuously determine whch constituents are present in the atmosphere and at what concentration. While it is appreciated that the electrodes measure ion activities, a calibration with known constituents can produce a final result which is the concentration of the constituents. The gases to be analyzed would have different elemental composition and these elements would form ions when dissociation of the compound occurs. This can happen even when low traces of water vapor are present as in the case of an atmospheric environment or when electrochemical forces such as an applied potential, e.g., <6 volts, provides energy sufficient for ionization. This latter procedure can be achieved in a scanning mode to provide the output potential information for the analysis by the microprocessor.

Additional qualitative information can be provided by the segment forming the redox electrode. Thus, chloride, fluoride, sulfide, etc. ion selective electrodes can be used to detect the presence of those various agents in the atmosphere. The chloride electrode may consist of a silver segment or a thin deposit of silver on a less expensive base metal by sputtering or other vacuum depositing methods. The surface of the silver can then be modified to measure chloride ion by treating it with hydrochloric acid which transforms the silver surface into silver chloride which is an excellent chloride ion selective electrode in conjunction with the metallic silver. Similarly, a sulfide electrode can be made by treating the silver surface with potassium sulfide or hydrogen sulfide. This will transform the surface into silver sulfide, which is effective to function a sulfide ion selective electrode. The silver sulfide, silver chloride, etc. can also be vacuum deposited selectively. The fluoride electrode can be produced by a lanthanum flouride deposit, while the arsenic electrode can be effected with an arsenic sulfide layer.

The redox electrode should preferably be made of platinum Such an electrode would be electrolytically coated with black platinum by the known methods. The electrolyte 24 could contain a small quantity of quinhydrin or other redox material. The electrolyte solvent for the electrolyte layer 24, which is preferably non-aqueous, can be chosen from among a number of well-known organic liquids with a low vapor pressure and compatibility with the material of the membrane 26 and the substrate 2 being requirements for longevity. Examples of nonaqueous solvents are phenylacetonitrile, ethylene glycol, DMSO and propylene carbonate. In addition to a conductive salt, other additives such as ionic strength adjustors and reference electrolytes could be added to the thin layer of electrolytic liquid.

The reference electrode can conveniently be made of a material whose ions are not expected to be found in the atmosphere to be analyzed. Such electrode materials could be cadmium, lead, mercury, zinc, copper, etc. with properly adjusted salt concentrations. Alternatively, the reference electrode could be made from a chemically inert metal, e.g., gold, platinum, etc. Since all potentiometric electrodes are temperature sensitive, and since their behavior is described by the well known Nernst equation, a thermistor element 34 or other temperature sensing devices is positioned in the electrode sensor, so that its output signal can also be utilized by the microprocessor to compensate for changes in temperature. The membrane 26 can be a silicon rubber membrane having an average one mil thickness which is effective to allow permeation by the constituents of interest while keeping most interferences at a low level. Other materials which may be used to provide selective penetration of constituents of interest are polycarbonate, ethylcellulose, cellulose acetate, polyvinyl chloride, copolymers, etc. Typical output signals from the electrode system which can be expected would be a 1 millivolt signal which is produced by a concentration of 375 micrograms per liter of air for the chloride electrode and about about 350 micrograms per liter of air for the sulfide electrode.

The advantages of this system described in this disclosure are principally an adaptability to extreme miniaturization including the microprocessor and any needed liquid crystal readout, e.g., wristwatch size, a low power consumption, e.g., two watts, versatility for providing an analysis of a great varity of gases and vapors, a generally rugged solid state construction with the exception of the thin layer electrolyte providing shock resistance for field use and a high selectivity governed by the electrode composition, the electrolyte and the membrane selectivity in addition to the redox measurements and the electrolytic ionization. The information provided by the sensor can be substantially continuously correlated by the microprocessor to provide a maximum speed of constituent identification to the wearer.

Accordingly, it may be seen that there has been provided, in accordance with the present invention, an improved electrochemical sensor.

The embodiments of the present invention in which an exclusive property or privilege is claimed are defined as follows:

1. An electrochemical sensor system comprising
 a chemically inert non-conductive substrate,
 a plurality of electrically conductive segments isolated from each other mounted on said substrate,
 a plurality of differing ion conductive sensing materials covering respective ones of said segments,
 at least one electrically conductive uncoated segment mounted on said substrate and isolated from said plurality of segments,
 a nonaqueous electrolyte layer covering all of said segments on said sensing materials and on said uncoated segment to form a sorption/desorption medium,
 a semi-permeable membrane means covering said electrolyte layer and contacting said substrate along a peripheral area emcompassing said electrolyte and
 a plurality of electrical conductors having one end attached to respective ones of said segments and a second end extending externally of said substrate and said membrane means.

2. A sensor as set forth in claim 1 wherein said ion conductive materials are selected to sense chlorine, fluorine, sulfide and arsenic.

3. A sensor as set forth in claim 1 wherein one of said segments is a redox electrode.

4. A sensor as set forth in claim 1 wherein said substrate includes a temperature sensitive element and said electrical conductors include a conductor means attached to said element.

5. A sensor as set forth in claim 1 wherein said electrolyte includes a solvent chosen from the group consisting of phenylacetonitrile, ethylene glycol, DMSO and propylene carbonate.

6. A sensor as set forth in claim 1 wherein said membrane is made from a material chosen from the group consisting of silicon rubber, polycarbonate, ethylcellulose, cellulose acetate and polyvinyl chloride.

7. A sensor as set forth in claim 1 wherein said substrate is made from a glass-filled epoxy.

8. A sensor as set forth in claim 1 wherein said membrane means includes an O-ring for securing said membrane means to an outer periphery of said substrate.

9. A sensor as set forth in claim 1 wherein said uncoated segment is arranged to be a reference electrode and is made from a material chosen from the group consisting of gold, platinum, cadmium, lead, mercury, zinc and copper.

10. A sensor as set forth in claim 1 wherein said electrolyte layer has a thickness of approximately one mil and is an organic liquid having a low vapor pressure and using a nonaqueous solvent chosen from the group consisting of phenylacetronitrile, ethylene glycol, DMSO and propylene carbonate.

* * * * *